US00PP13118P2

(12) United States Plant Patent
Klemm

(10) Patent No.: US PP13,118 P2
(45) Date of Patent: Oct. 22, 2002

(54) CALIBRACHOA PLANT NAMED 'KLEC00071'

(75) Inventor: Nils Klemm, Stuttgart (DE)

(73) Assignee: Klemm & Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 09/904,714

(22) Filed: Jul. 16, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Calibrachoa plant named 'KLEC00071', characterized by its compact and cascading plant habit; freely branching habit; early and freely flowering habit; red purple-colored flowers; and good weather tolerance.

1 Drawing Sheet

BOTANICAL CLASSIFICATION

Calibrachoa sp. cultivar KLEC00071.

BACKGROUND OF THE INVENTION

The present Invention relates to a new and distinct cultivar of Calibrachoa plant, botanically known as Calibrachoa sp., and hereinafter referred to by the name 'KLEC00071'.

The new Calibrachoa is a product of a planned breeding program conducted by the Inventor in Stuttgart, Germany. The objective of the program is to create new early-flowering Calibrachoa cultivars with cascading and freely branching growth habit and attractive flower colors.

The new Calibrachoa originated from a cross made by the Inventor during the summer of 1997 of a proprietary selection of Calibrachoa identified as code number J 101, not patented, as the female, or seed, parent with a proprietary selection of Calibrachoa identified as code number J 353, not patented, as the male, or pollen, parent. The new Calibrachoa was selected by the Inventor in May, 1998 in a controlled environment in Stuttgart, Germany, on the basis of its cascading plant habit and red purple-colored flowers.

Asexual reproduction of the new cultivar by terminal cuttings taken in a controlled environment in Stuttgart, Germany since June, 1998, has shown that the unique features of this new Calibrachoa are stable and reproduced true to type in successive generations.

SUMMARY OF THE INVENTION

Plants of the cultivar KLEC00071 have not been observed under all possible environmental conditions. The phenotype may vary somewhat with variations in environment such as temperature, light intensity, daylength, water status and fertility level without, however, any variance in genotype.

The following traits have been repeatedly observed and are determined to be the unique characteristics of 'KLEC00071'. These characteristics in combination distinguish'KLEC00071' as a new and distinct cultivar of Calibrachoa:

1. Compact and cascading plant habit.
2. Freely branching habit.
3. Early and freely flowering habit.

4. Red purple-colored flowers.
5. Good weather tolerance; tolerant to rain and low and high temperatures.

Plants of the new Calibrachoa differ primarily from plants of the female parent selection, J 101, in flower color as flower color of plants of the new Calibrachoa is red purple whereas flower color of plants of the female parent selection is violet purple. In addition, plants of the female selection flower earlier than plants of the new Calibrachoa. Plants of the new Calibrachoa differ primarily from plants of the male parent selection, J 353, in flower size as plants of the new Calibrachoa have smaller flowers than plants of the male parent selection.

Plants of the new cultivar can be compared to plants of the Calibrachoa cultivar Trailing Pink, not patented. In side-by-side comparisons conducted by the Inventor in Stuttgart, Germany, plants of the new Calibrachoa differed from plants of the cultivar Trailing Pink in the following characteristics:

1. Plants of the Calibrachoa are more stocky than plants of the Trailing Pink.
2. Plants of the new Calibrachoa have smaller leaves than plants of the Trailing Pink.
3. Plants of the new Calibrachoa flower earlier than plants of the Trailing Pink.
4. Plants of the new Calibrachoa have larger flowers than plants of the cultivar Trailing Pink.

Plants of the cultivar KLEC00071 can also be compared to plants of the Calibrachoa cultivar Cluster Pink, not patented. However in side-by-side comparisons conducted by the Inventor in Stuttgart, Germany, plants of the new Calibrachoa and the cultivar Cluster Pink differ in the following characteristics:

1. Plants of the new Calibrachoa are more cascading than plants of the cultivar Cluster Pink.
2. Plants of the new Calibrachoa have smaller flowers than plants of the cultivar Cluster Pink.
3. Flower color of plants of the new Calibrachoa is slightly darker than flower color of plants of the cultivar Cluster Pink.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa. The photograph comprises a side perspective view of a typical plant of 'KLEC00071' grown in a hanging basket container.

DETAILED BOTANICAL DESCRIPTION

In the following description, color references are made to The Royal Horticultural Society Colour Chart except where general terms of ordinary dictionary significance are used. Plants grown in 12-cm containers were used for following description. Plants were grown under conditions which closely approximate commercial production conditions from January to May in Stuttgart, Germany in polyethylene-covered greenhouses. Plants used for the description and the photographs were about four months from planting rooted cuttings. During the production period, day and night temperatures ranged from about 10 to 18° C. and light levels were about 20,000 lux during the beginning of the production period increasing to 50,000 lux towards the end of the production period.

Botanical classification: Calibrachoa sp. cultivar KLEC00071.

Parentage:

*Female parent*.—Proprietary selection of Calibrachoa sp. identified as J 101, not patented.

*Male parent*.—Proprietary selection of Calibrachoa sp. identified as J 353, not patented.

Propagation:

*Type cutting*.—Terminal vegetative cuttings.

*Time to initiate and develop roots*.—Summer: About 21 days at 20 to 26° C. Winter: About 28 days at 20° C.

*Root description*.—Numerous, fine, fibrous, well-branched, white in color.

Plant description:

*Form*.—Annual flowering plant; initially upright to semi-upright then cascading; uniform, flattened and mounded appearance.

*Usage*.—Appropriate for hanging baskets, window boxes and patio containers.

*Plant height* (*from soil level to top of plant plane*).—About 5 cm.

*Plant diameter* (*area of spread*).—About 40 cm.

*Growth rate*.—Relatively moderate.

*Branching habit*.—About 6 to 8 lateral branches per plant; pinching is typically not required.

*Lateral branch description*.—Length: About 20 cm. Diameter: About 1.3 to 1.7 cm. Internode length: About 5 to 15 mm. Texture: Smooth, glabrous. Color: 145A.

*Foliage description*.—Leaves simple, generally symmetrical and long persisting; sessile. Arrangement: Alternate. Length: About 1 to 2 cm. Width: About 6 to 9 mm. Shape: Elliptic. Apex: Broadly acute. Base: Attenuate. Margin: Entire. Texture: Smooth, glabrous. Venation pattern: Pinnate. Color: Young foliage, upper surface: 141A. Young foliage, lower surface: 143A. Mature foliage, upper surface: 137A. Mature foliage, lower surface: 137D. Venation, upper and lower surfaces: 145A.

Flower description:

*Flower type and habit*.—Flowers face somewhat upright or outward; single, axillary; salverform. Flowers not persistent. Very freely flowering with about 20 to 25 flowers per lateral stem. Faint fragrance.

*Natural flowering season*.—Spring until frost in the autumn; flowering continuous.

*Time to flower*.—Early flowering; plants begin flowering about 11 weeks after planting.

*Flower longevity on the plant*.—About 7 days.

*Flower size*.—Diameter: About 2.5 to 3 cm. Tube length: About 1.2 cm. Throat diameter, distal end: About 6 mm. Tube diameter, proximal end: About 1 to 2 mm.

*Flower buds* (*before showing color*).—Length: About 7 mm. Diameter: About 2 mm. Shape: Roughly oblong. Color: 149C.

*Corolla*.—Arrangement/appearance: Single whorl of five petals, fused into flared trumpet. Petal length from throat: About 9 to 12 mm. Petal width: About 1 to 1.2 cm. Petal shape: Roughly spatulate with cordate apex. Petal margin: Entire. Petal texture: Smooth, glabrous; velvety. Color: Petal, upper surface, when opening: 74A. Petal, lower surface, when opening: 78C. Petal, upper surface, opened flower: 74B, flower color fading to 78B with subsequent development; venation, 88A. Petal, lower surface, opened flower: 77C; venation, 184A. Flower throat (inside): 160A; venation, 184A. Flower tube (outside): 88A; venation, 88A.

*Sepals*.—Arrangement/appearance: Single whorl of five sepals, star-shaped. Length: About 1.6 cm. Width: About 3 mm. Shape: Lanceolate. Apex: Acute. Margin: Entire. Texture: Smooth, glabrous. Color: Upper surface: 138A. Lower surface: 138B.

*Peduncles*.—Length: About 1.7 to 2 cm. Width: About 2 mm. Strength: Moderately strong. Angle: Erect to about 15° from vertical. Texture: Smooth, glabrous. Color: 145A.

*Reproductive organs*.—Stamens: Quantity: Five per flower. Anther shape: Elliptic. Anther length: About 1 to 2 mm. Anther color: 11B. Pollen amount: Scarce. Pollen color: 11B. Pistils: Quantity: One per flower. Pistil length: About 7 mm. Stigma shape: Oval. Stigma color: 149A. Style length: About 5 mm. Style color: 150A. Ovary color: 154A.

*Seed*.—Seed production has not been observed.

Disease resistance: Plants of the new Calibrachoa have not been noted to be resistant to Powdery Mildew.

Weather/temperature tolerance: Plants of the new Calibrachoa are tolerant to rain and wind and have been observed to tolerate temperatures from 1 to 50° C.

It is claimed:

1. A new and distinct cultivar of Valibrachoa plant named 'KLEC00071', as illustrated and described.

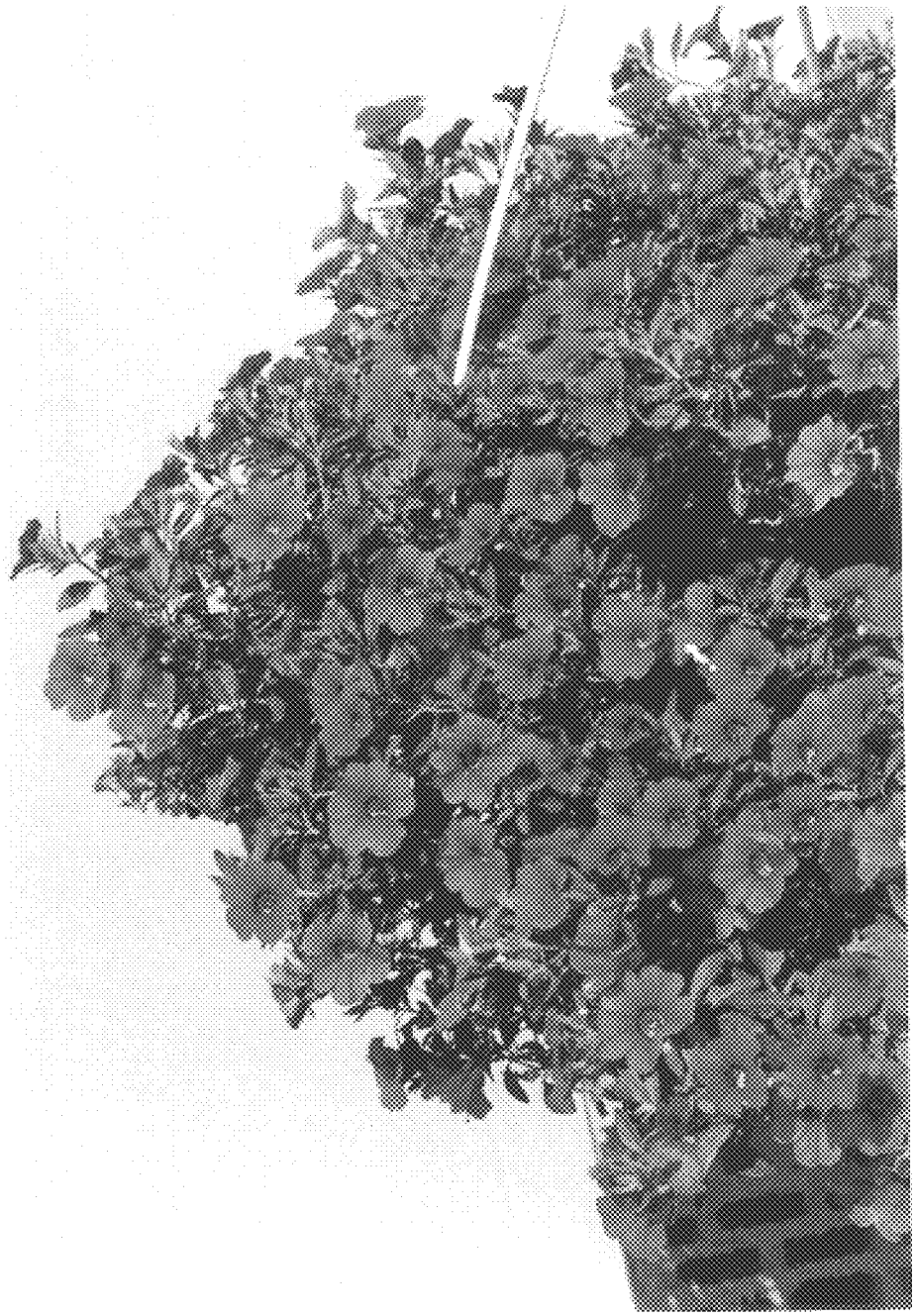

* * * * *